United States Patent
Jaeger (10) Patent No.: US 7,798,960 B2
(45) Date of Patent: Sep. 21, 2010

(54) SPECULUM

(75) Inventor: John C. Jaeger, 3584 Batavia-Elba TLR, Oakfield, NY (US) 14125

(73) Assignee: John C. Jaeger, Batavia, NY (US)

( * ) Notice: Subject to any disclaimer, the term of this patent is extended or adjusted under 35 U.S.C. 154(b) by 1216 days.

(21) Appl. No.: 10/773,346

(22) Filed: Feb. 9, 2004

(65) Prior Publication Data

US 2005/0250993 A1  Nov. 10, 2005

(51) Int. Cl.
*A61B 17/06* (2006.01)

(52) U.S. Cl. ..................................... 600/224

(58) Field of Classification Search ............... 600/184, 600/185, 186, 190, 191, 193, 196, 197, 201, 600/208, 209, 210, 213, 214, 215, 216, 217, 600/218, 219, 220, 222, 224, 225, 226, 227, 600/231, 232, 233, 234, 235
See application file for complete search history.

(56) References Cited

U.S. PATENT DOCUMENTS

| | | | | |
|---|---|---|---|---|
| 447,761 A * | 3/1891 | Clough | ...................... | 600/224 |
| 475,975 A * | 5/1892 | Clough | ...................... | 600/224 |
| 2,751,903 A * | 6/1956 | Ivory et al. | .................. | 600/216 |
| 3,509,873 A * | 5/1970 | Karlin et al. | ................. | 600/226 |
| 3,724,449 A * | 4/1973 | Gauthier | ..................... | 600/215 |
| 3,965,890 A * | 6/1976 | Gauthier | ..................... | 600/215 |
| 4,206,750 A | 6/1980 | Kaivola | ........................ | 128/17 |
| 5,072,720 A | 12/1991 | Francis et al. | ................. | 128/17 |
| 5,293,863 A * | 3/1994 | Zhu et al. | .................... | 600/214 |
| 5,336,228 A | 8/1994 | Cholhan | .................... | 606/119 |
| 5,505,690 A * | 4/1996 | Patton et al. | ................ | 600/210 |
| 5,545,122 A | 8/1996 | Spruill | ....................... | 600/222 |
| 5,873,820 A | 2/1999 | Norell | ........................ | 600/220 |
| 5,916,151 A | 6/1999 | Charters | ..................... | 600/224 |
| 5,980,534 A | 11/1999 | Gimpelson | .................. | 606/119 |
| 5,993,461 A | 11/1999 | Abae | ........................... | 606/119 |
| 6,416,467 B1 | 7/2002 | McMillin et al. | ............ | 600/224 |
| 6,436,033 B2 | 8/2002 | Tan | ............................ | 600/224 |
| 6,450,952 B1 | 9/2002 | Rioux et al. | ................ | 600/223 |

* cited by examiner

*Primary Examiner*—Anu Ramana
(74) *Attorney, Agent, or Firm*—Novak Druce + Quigg LLP (57) ABSTRACT

A speculum for the insertion and expanding of a body cavity. The speculum comprises a plurality of blades pivotally connected around a ring-shaped frame, the first ends thereof extending longitudinally and meeting at a point distant from the frame to form a generally bulbous end and the second ends which are manipulated to rotate the blades about the frame. A rotating action of the second ends causes the first ends to angularly move away from each other to expand the bulbous end, and hence the body cavity. A series of block pivotally attached to the frame interact with the second ends to form a ratcheting locking means to lock the blades at certain positions between a closed position and an open position.

9 Claims, 8 Drawing Sheets

SPECULUM

This invention relates to specula that are inserted into body cavities and manipulated to spread or open the cavity for observation.

BACKGROUND OF THE INVENTION

Specula are used to examine interior portions of a body through cavities. The specula is placed into the cavity and expanded to open the cavity while at the same time permitting a physician to view the inside of the cavity. Various types and designs of specula are well known. A typical type is disclosed in U.S. Pat. No. 5,072,720, wherein a pair of duck-bill blades are slidably attached to each other. The blades are inserted into a body cavity and manipulated to move the blades apart from each other to form a cavity therebetween. The physician then views the cavity walls through a space formed between the blades.

Another design for a speculum is disclosed in U.S. Pat. No. 5,916,151, wherein four blades spaced apart are connected by cables to a pair of rings, at a center portion thereof and an end portion. The distal ends of the blades are generally in a side by side relationship and movable laterally with respect to each other between a contracted position wherein the distal ends are closely adjacent to each other to an expanded condition wherein the blades are separated from each other. The blades are placed into the body cavity in the contracted position and then manipulated, via the cables, to the extended condition to open up the cavity.

While these specula perform satisfactorily in most conditions, their insertion and manipulation can cause discomfort to the patient. The disadvantage of the older duck-bill type specula is that the peripheral edge of the blades can cause discomfort during insertions and removals. Such blades can also pinch interior walls when the blades are moved back together during removal of the speculum following an observation by the physician.

A disadvantage with the four blade design is that the blades hang loose in the cables, where it is possible for one or more of the blades to extend in undesired directions during insertion or during manipulation causing discomfort. Such a design requires the physician to manually hold the blades together during insertion and monitor closely the positions of the blades.

SUMMARY OF THE INVENTION

It is therefore an object of the present invention to overcome these and other problems in the prior art by providing a speculum that is compact, easy to insert into the cavity and manipulate, which together will provide less discomfort to the patient than prior specula.

The speculum according to the invention comprises a plurality of blades positioned generally parallel to each other and hinge coupled to a frame at points in between their end sections. In a closed position, first end sections of the blades meet adjacent each other at a distal end from the frame. Spring mechanisms bias the first end sections of the blades towards each other. Between the first end sections and the frame, the blades define a generally cylindrical envelope with a bulbous end. The cylindrical envelope created by the first end section can then be inserted into the body cavity. The bulbous end prevents easy removal of the speculum from the cavity. Upon rotation of the blades about the hinge against the action of the springs, the first ends of the blades move away from each other to increase the cavity there between. Such movement of the blades into an open position changes the cylindrical envelope into more of a conical envelope, and hence increases the body cavity size to allow for viewing of the body cavity walls from outside the cavity.

In a preferred embodiment, the speculum has a locking mechanism comprising ratcheting blocks which act in conjunction with second ends of the blades located on the ends opposite the first ends. The blocks are connected to the frame by means of pins. Springs bias the blocks into contact with the seconds ends. A series of stops on sides of the blocks contacts the second ends and prevents a closing action of the blades. Each stop holds the respective blade at a certain amount of rotation about the hinge, thus allowing the speculum to be maintained at varied open positions. A rotation of the blocks against their respective biasing springs releases the blades to close the blades.

The frame has generally an annular shape with a hollow center. In a preferred embodiment, the blades are hinged at an outer surface of the disc, the first ends extending through the center of the frame. When the blades are in open positions and first ends of the blades are separated from each other, the physician is able to look through the center of the frame and observe the cavity into which the first ends of the speculum are placed.

Such a novel and improved speculum can be used in a variety of services, particularly vaginally during gynecologic procedures, including endoscopic Pap tests, endoscopic colposcopy, tissue biopsy, cryotherapy, loop electroexcision and other procedures. The speculum according to this invention will cause minimal distention of the female pelvic floor while providing satisfactory distention and thus exposure for examination of the upper vagina and cervix.

BRIEF DESCRIPTION OF THE DRAWINGS

The invention will now be described in detail in conjunction with several drawings, in which.

DETAILED DESCRIPTION OF THE INVENTION

The preferred embodiment of the invention is shown in FIGS. 1-5. As shown in the figures, the speculum 1 has a generally elongated shape, consisting of an insertion end 10, extending towards a front end of the speculum and a control end 20, extending to a rear of the speculum. The speculum comprises four blades (three visible in the figure) 110, 120, 130 and 140 extending from a frame member 100. The blades have first sections 115, 125, 135 and 145 extending forward in the front end 10 of the frame and second sections 116, 126, 136 and 146 extending behind the frame in the control end 20. Each of the blades is attached to the frame via hinges 150, 151, 152 and 153 (three shown), which provides for rotation of the blades with respect to the frame and each other.

Figure 2:
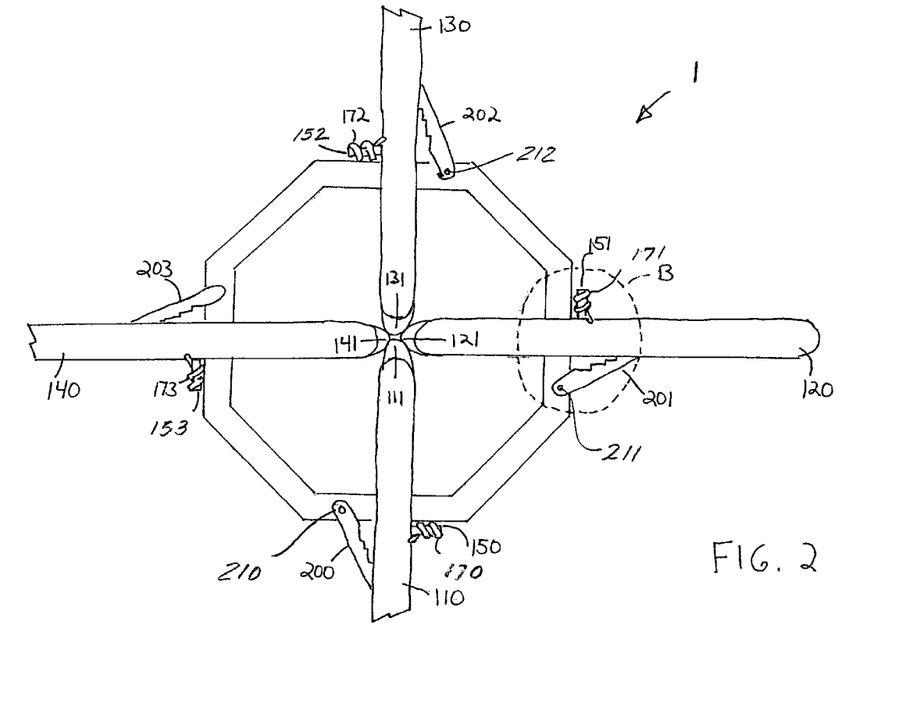
FIG. 2 is a bottom side view of the speculum shown in FIG. 1.

As shown in the figures, particularly, FIG. 2, the frame 100 has a generally octagonal shape with an opening forming a hollow center, however, other shapes for the ring may be used, such as circular, triangular, rectangular, etc., depending on the particular design of the speculum or the number of blades required for the speculum, and as long as the center of shape is open. The octagonal shape is shown as an example. The hinges 150, 151, 152 and 153 that attach the blades 110, 120, 130 and 140 to the frame 100 are located on the outer surface thereof. The first sections 115, 125, 135 and 145 of the blades then extend through the center of the frame 100 and extend in the forward direction to form the insertion end 10.

Figure 1:
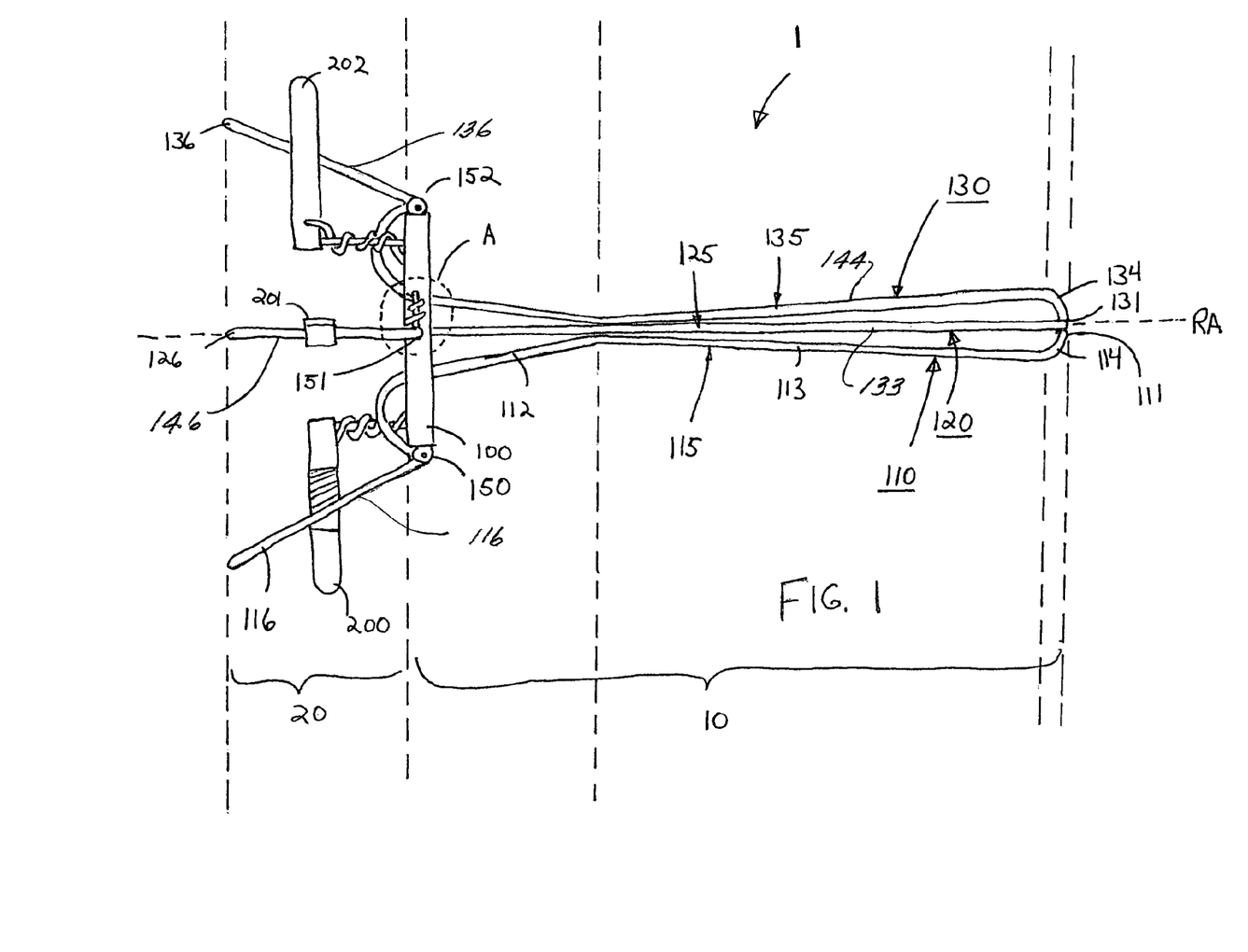
FIG. 1 is a side view of the speculum according to this invention.

Each blade is generally divided into four sections, for example, with respect to blade 110, the second section 116 is one section and the first section 115 is divided into three sections, namely a neck portion 112, an intermediate portion 113 and an end portion 114. Each blade has similar features. The end portion 114 is at the front of the speculum and has a curved shape and a tip 111 that abuts a central axis RA extending from the center of the frame 100. Each of the other blades 120, 130 and 140 have such a curved shape end portion 124, 134 and 144 and each blades' tips 121, 131, and 141 abuts each other at the central axis, as shown in FIG. 2. Such features provide a generally rounded end for the speculum, which is shown in FIG. 1, to allow for an easy insertion of the first sections 115, 125, 135 and 145 into a body cavity and reducing discomfort to the patient.

The neck portion 112 of blade 110 extends from the hinge 150 to the intermediate portion 113. As the neck portion passes through the center of the frame 100, it begins to converge on the central axis RA. Each of the other blades has a similar neck portion that converges on the central axis RA. The grouping of the neck portions forms a generally conical shape.

The intermediate section 113 extends between the neck portion 112 and the end portion 111 of blade 110. The intermediate section 113 at the neck portion begins near the central axis RA and extends away until it connects to the end portion 111. The intermediate sections 123, 133 and 144 of the other blades have a similar design. The combination of these intermediate sections provides a generally bulbous end to the insertion end 10. The bulbous end aids in maintaining the insertion inside the cavity.

Figure 4:
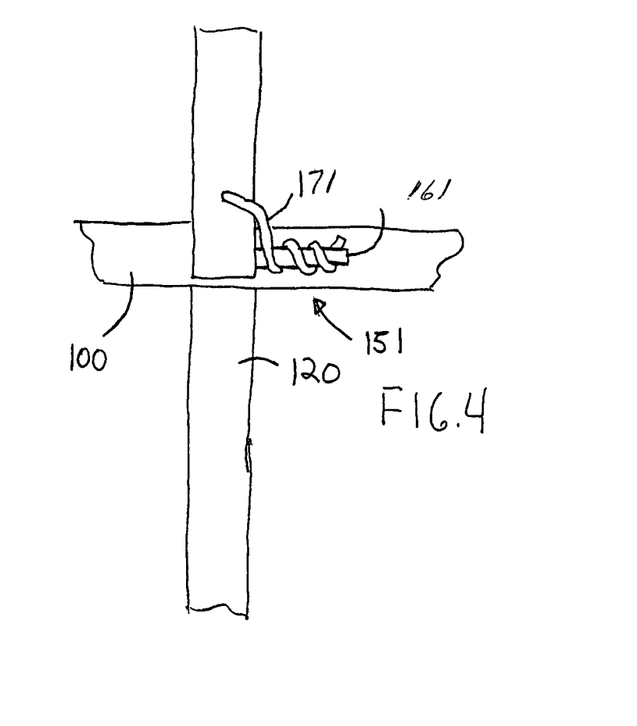
FIG. 4 is an enlargement of section B of FIG. 2.

The hinges 150, 151, 152 and 153 between the blades 110, 120, 130 and 140 and the frame 100 are shown in detail in FIGS. 2 and 4. FIG. 4 is a blown up view of hinge 151 between blade 120 and frame 100. The hinge 151 consists of a hinge pin 161 which is attached to frame 100. The blade 120 fits over the pin 161 and rotates about the pin. A hinge spring 171 is connected between the frame 100 and blade 120 to bias blade 120 to rotate in a certain direction (discusses below). Each blade has similar hinge pins 161, 162 and 163 and hinge springs 170, 172 and 173 designs, as shown in FIG. 2. While the hinge pins here are shown and disclosed attached to the frame, they may alternatively be attached to the blade. Either or other designs may be used as long as the blades hinge about the frame.

Figure 6:
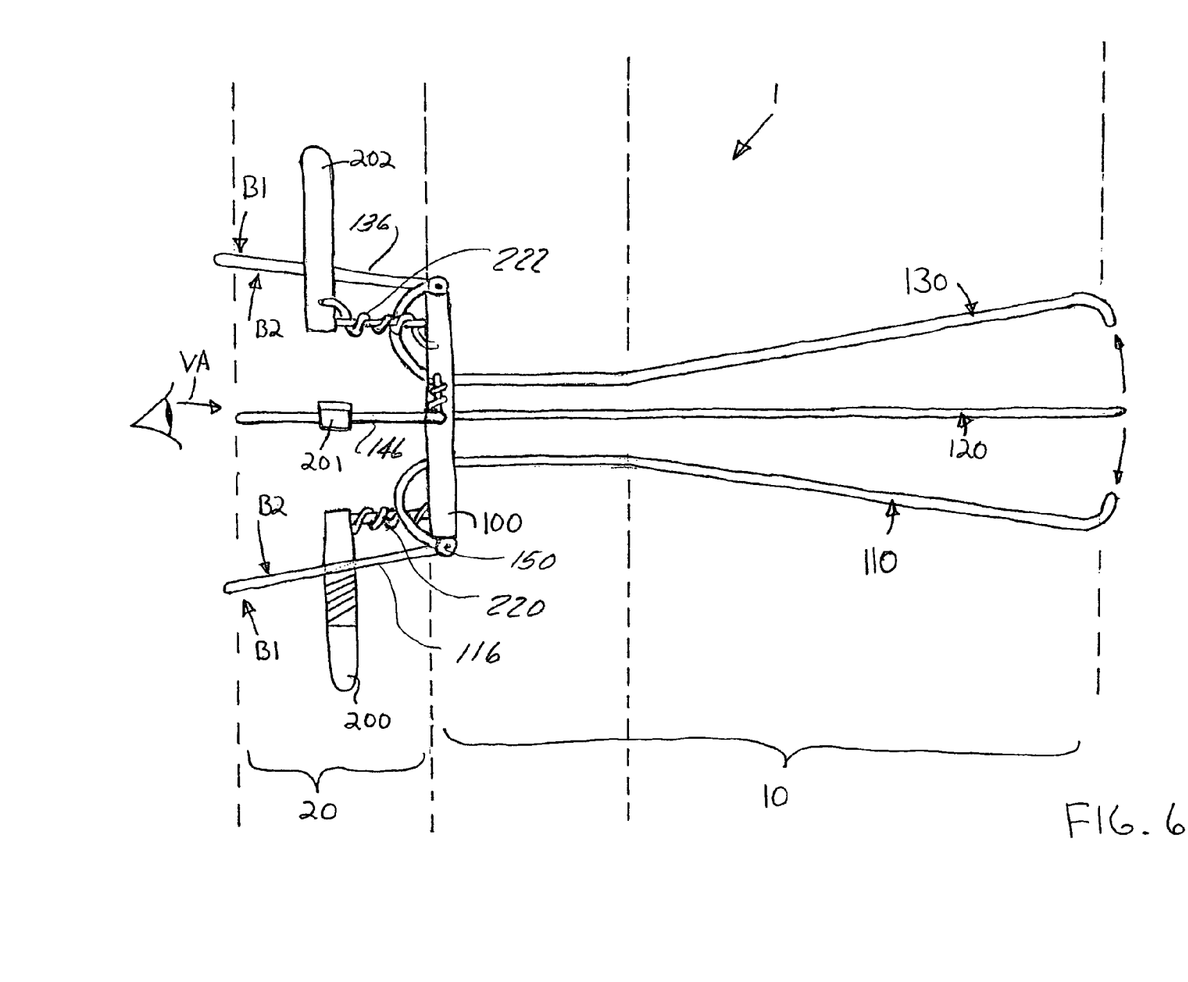
FIG. 6 is another side view of the speculum shown in FIG. 1 in an open position.

The second sections 116, 126, 136 and 146 extend in a direction generally behind the frame in the control end 20 and attach to the first sections 115, 126, 136 and 146 at the hinges 150, 151, 152 and 153. A physician using the speculum manipulates the second sections to operate the speculum. As shown in FIG. 6, pressure along line B1 towards the central axis RA against the second section 116 of blade 110 causes the blade to rotate about hinge 150. During the rotation, the end portion 114 begins to move away from the central axis RA.

Figure 7:
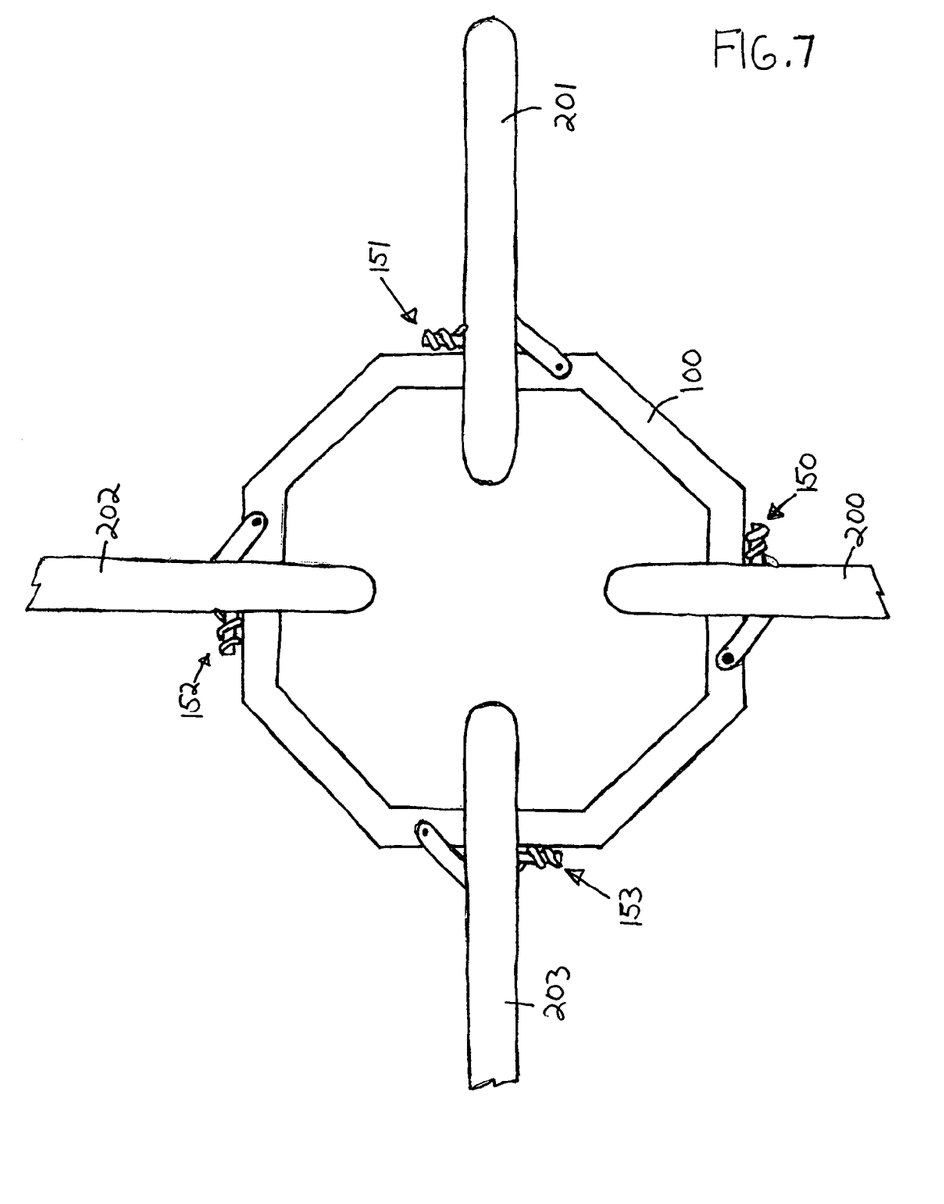
FIG. 7 is a bottom view of the speculum shown in FIG. 6.
Figure 8:
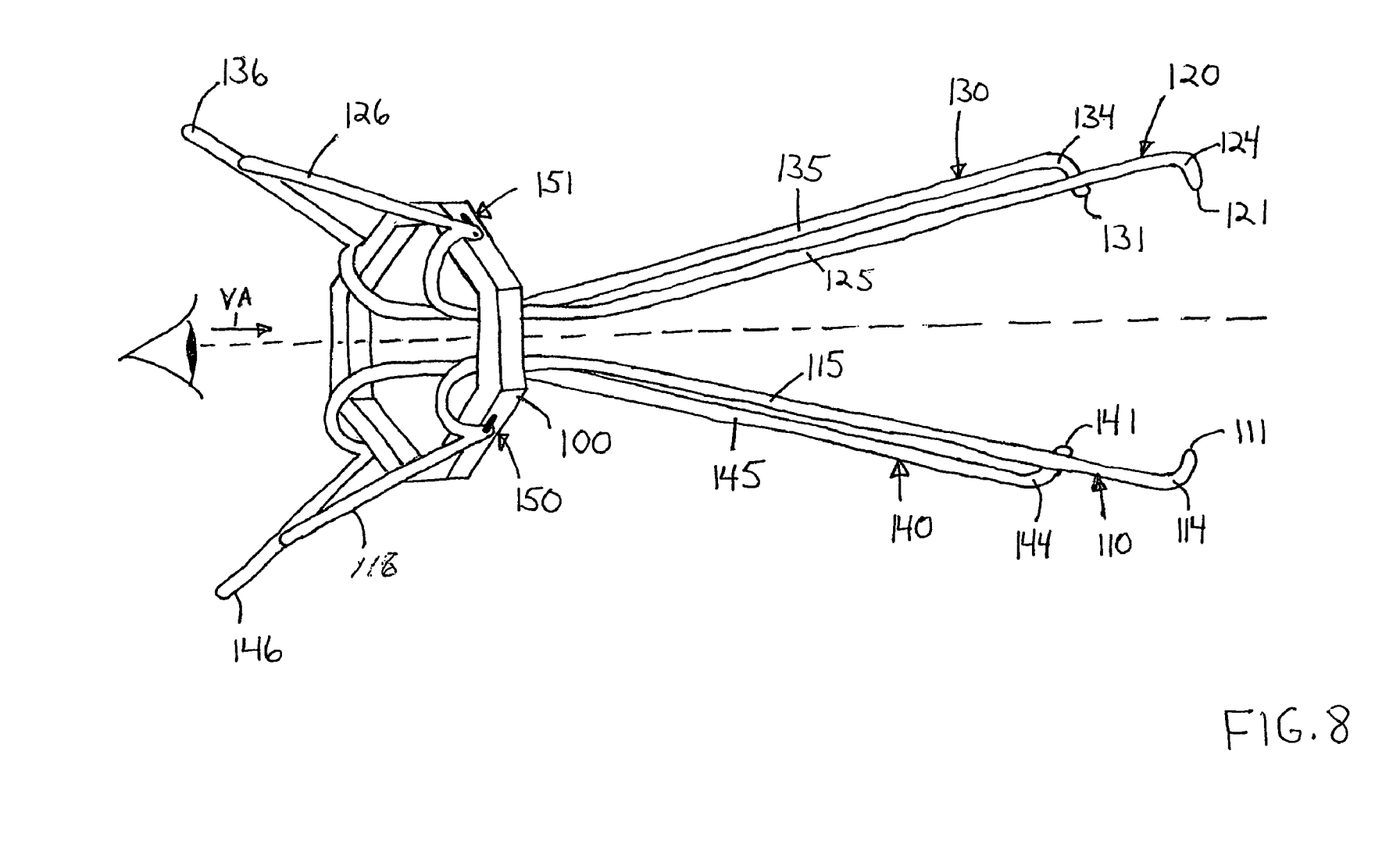
FIG. 8 is a perspective view of a speculum according to this invention.

A similar event occurs when each of the second sections 126, 136 and 146 of blades 120, 130 and 140 are pushed or pulled towards the central axis RA. Such actions cause each of the end portions 124, 134 and 144 to move away from the central axis RA. This causes the insertion end 10 of the speculum 1 to move into an open position with the blades apart, as shown in FIG. 8 allowing for the body cavity to be opened up. In the full open position (shown), the neck portions of each of the blades are no longer in a conical shape, but rather are parallel to each other and parallel to the central axis RA. These features of the open position along with the open center of the frame allow for a physician to view along center axis RA, as shown in FIGS. 6 and 8 along line VA, the inside of the body cavity opened up by the speculum. The view is shown in FIG. 7.

Upon release of the pressure against the second sections 116, 126, 136 and 146, the blades rotate back in the direction B2 towards the closed position, as shown in FIGS. 1 and 2 through the action of the springs 170, 171, 172 and 173 at the respective hinges 150, 151, 152 and 153. Thus, the end portions 111, 121, 131 and 141 are biased and move towards center axis RA so that the blades, and hence the insertion end, move to the closed position.

In another embodiment of the invention, the speculum is provided with a locking mechanism to hold the speculum at various positions between the closed position and the open position. Such mechanisms are shown in FIGS. 1, 2, 3 and 5. The mechanisms comprise a series of blocks 200, 201, 202 and 203 which interact with the second sections 116, 126, 136 and 146 of the blades. The blocks are pivotally connected to the frame 100 via block pins 210, 211, 212 and 213 to allow rotation of the blocks in a direction generally perpendicular to the central axis. Block springs 220, 221, 222 and 223 mounted between the blocks and the frame around the pins bias the blocks to rotate in a certain direction.

Figure 3:
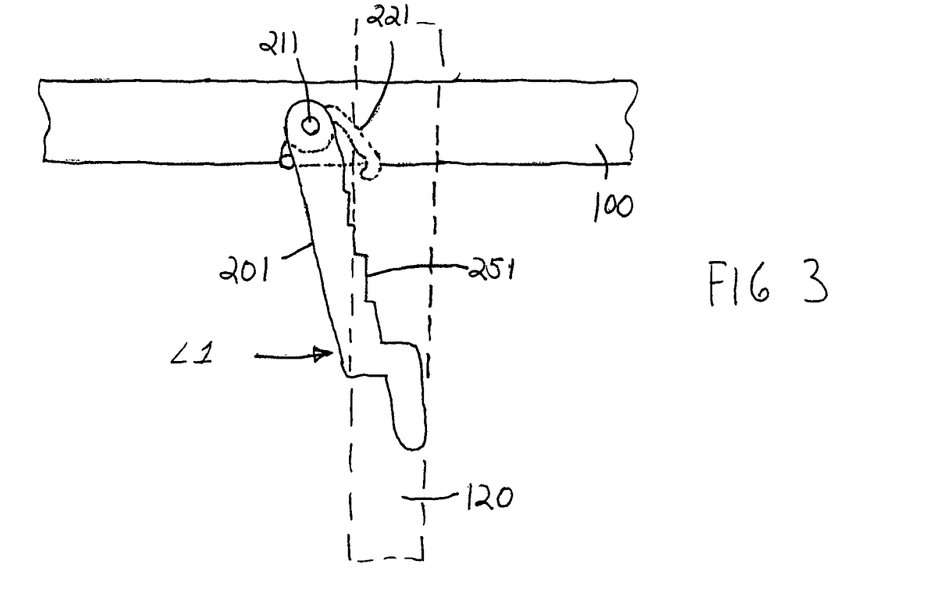
FIG. 3 is an enlargement of section A of FIG. 1.
Figure 5:
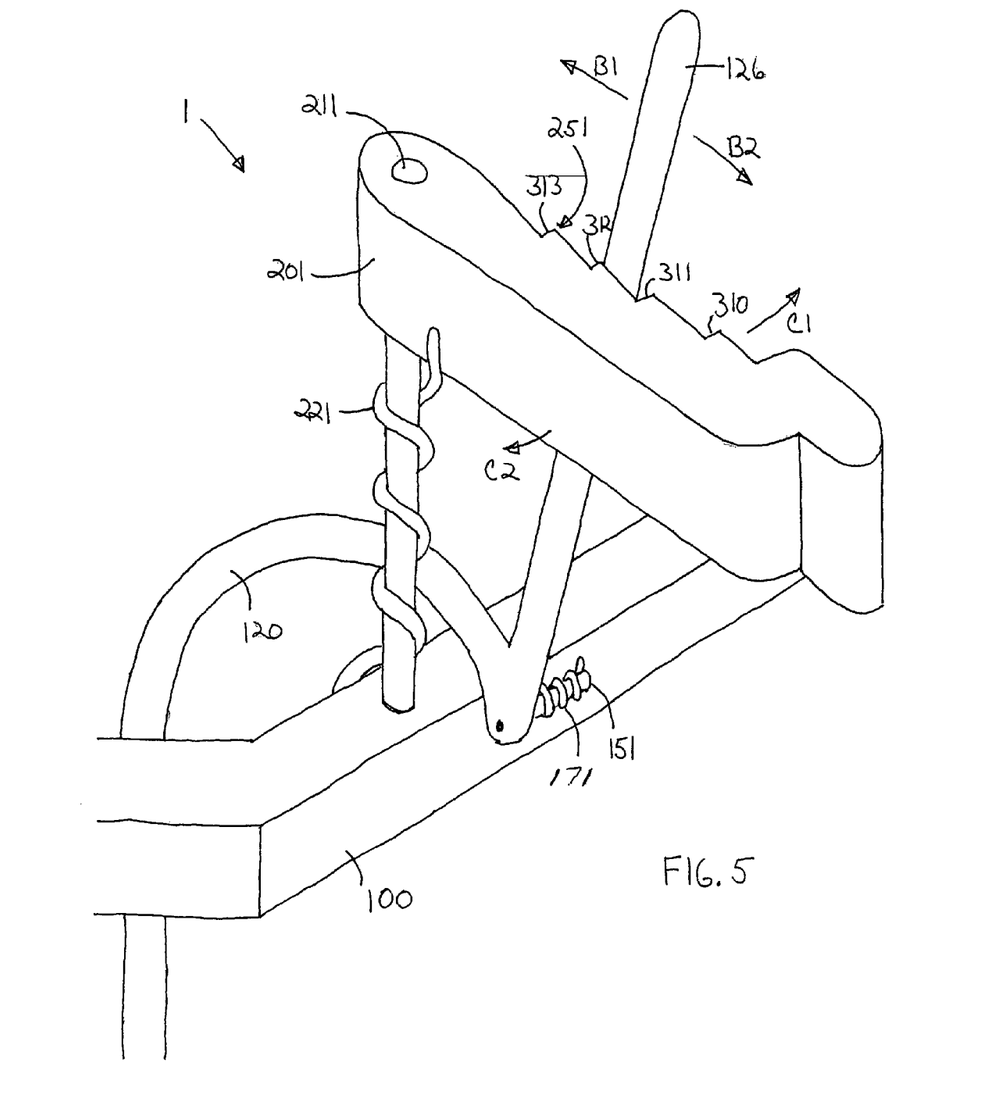
FIG. 5 is a perspective view of the hinge and locking mechanism of the speculum shown in FIG. 1.

In the detail shown in FIGS. 3 and 5, blade 120 is shown in conjunction with locking mechanism block 201. As shown, the block rotates about pin 211, generally perpendicular to the rotation of blade 120. The rotation is biased from block spring 221 to rotate in the direction of arrow L1 and press surface 251 against the second section 126 of blade 120. A series of stops 310, 311, 312 and 313 along the surface 251 provide locking contacts. When the second section is rotated inward along in the direction B1, the second section moves past the stops. The block spring 211 pushes the block against the second section causing it to click over the stops. When the pressure moving the second section in the direction B1 is ceased, hinge spring 171 biases the second section 120 in the direction B2, however, the last stop the second section passed prevents movement of the second section past that last stop. For example, in FIG. 5, the second section had last passed stop 311. Upon the cessation of the pressure against the second section in the direction B1, the hinge spring would bias the second section against stop 311, which prevents the second section from moving further in the direction B2, towards the closed position of the speculum. This action thus, locks the second section in the stop 311 position, holding the blade in the open position.

To unlock the locking mechanism to release the second section and allow it to return in the direction B2 towards the speculum closed position, the block 201 is rotated in the direction C2, which pulls the stops 310, 311, 312 and 313 away from the second section, allowing it uninterrupted movement in the direction B2 until is arrives at the closed position.

Similar locking mechanisms are provided using blocks 200, 202 and 203 in conjunction with their respective block pins and block springs and such locking mechanisms lock the release their respective second sections in a similar manner.

In operation of the speculum, by either a physician or otherwise, the speculum is held at the control end. The action of the hinge springs 170, 171, 172 and 173 bias the insertion end 10 of the speculum 1 in the closed position, as shown in FIG. 1. The closed position allows for easy insertion of the insertion end 10 into the body cavity without difficulty and causing little discomfort. The insertion end 10 is inserted into the cavity until the frame nearly abuts the rim of the body cavity or until the rim of the body cavity nears the portions of the blades between the neck portions and the intermediate portions.

The physician then manipulates each of the second sections 116, 126, 136 and 146 of the blades by moving them in the direction B1 towards the central axis RA of the frame. Such action causes the first sections 115, 125, 135 and 145 of the blades to begin to separate and open the insertion end 10 inside the body cavity. As the physician continually rotates the second sections, they continually click past stops on the locking blocks 200, 201, 202 and 203, which are biased against them. When either the physician has fully opened the speculum or the first sections are opened as far as the body cavity will allow, the physician simply releases or ceases further rotation of the second sections in the direction B1. The speculum has then been put into the open position which opens the body cavity. The hinge springs 170 171, 172 and 173 will then cause the second sections to rotate in the direction B2 until the second sections move into contact with the last stops on the locking blocks each passed. The stops will hold the respective second sections in place.

At this point, the physician can release the speculum and begin to take the proper tests within the cavity or view the cavity through the speculum. Such can be done by simply passing instruments through the frame center or by looking through the frame into the cavity which is opened up by the first sections.

When the physician has completed necessary actions and desires to remove the speculum, the blocks are simply rotated in the direction C2 to pull the stops away from the second sections, which releases the second sections and allows them to freely move in the direction B2 until the insertion end 10 of the speculum reaches the closed position under the action of the hinge springs. Once the speculum returns to the closed position, it can be removed from the body cavity.

Figure 9A:
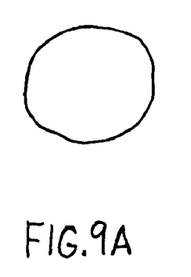
FIGS. 9A-9D are cross sections of alternate blade designs.
Figure 9B:
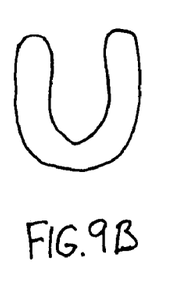
Figure 9C:
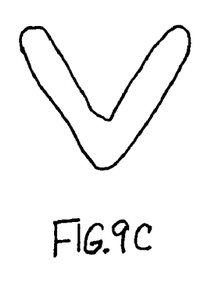
Figure 9D:
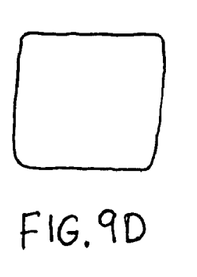

From the forgoing description, it is evident that there are a number of changes, modifications or alterations that can come within the province of a person having ordinary skill in the art. For example, this specification discloses a blade design that is round in shape, as shown in FIGS. 8 and 9A, however, various other designs are possible. For example, the blades may be of a u-shape as shown in FIG. 9B, a v-shape as shown in FIG. 9C or a rounded square shape as shown in FIG. 9D. Other possibilities are also possible depending on the particular design of the speculum and the material used for the blades. It is evident that any such changes, modification or alterations are specifically included in this description and this invention should only be limited by the claims following hereinafter.

I claim:

1. An instrument insertable in a body cavity for dilating said cavity comprising:
a frame having an opening through a centerline thereof;
a set of blades circumferentially spaced relative to said centerline, each having a first end projecting beyond a first side of said frame section, a second end section projecting beyond a second side opposite said first side of said frame and an intermediate section pivotally connected to said frame for pivotal movement relative to said frame in a plane including said centerline;
means operatively interconnecting said blades and said frame biasing the first ends of the blades together into abutting relation; and
means directly mounted on said frame and operatively engageable with said blades for biasingly restraining the pivotal movement of said blades,
whereby with said first end sections biased together, said engaging first end sections may be inserted into said cavity with said frame disposed in the exterior thereof, said second end sections may be drawn together against the biasing action of said first mentioned biasing means to cause a separation of said first end sections and thus dilate said cavity to permit visual access to said cavity through said frame, with said restraining means biasingly maintaining said first end sections apart, and upon completion of any procedure with which said instrument is used, said restraining means may be overcome to cause said first end section to pivot into engagement with one another to permit said first end sections of said instrument to be withdrawn from said cavity.

2. An instrument according to claim 1 wherein outer surfaces of the first end sections of said blades are provided with merging and contoured surfaces which cooperate when said first end sections engage to provide an elongated object with smooth surfaces facilitating the insertion and removal of said engaged first end sections into and out of said cavity.

3. An instrument according to claim 1 wherein each of the end sections of each of said blades is disposed at an angle relative to the intermediate section thereof.

4. An instrument according to claim 1 wherein said means for biasing the first ends of said blades together into abutting relation comprises a set of springs each interconnecting said a blade and said frame.

5. An instrument according to claim 1 wherein said means biasingly restraining said pivotal movement of said blades comprises a set of blocks each block supported on said frame and biased into engagement with a surface of one of said blades.

6. An instrument according to claim 5 wherein each of said blocks is provided with a surface of a nonplanar configuration engaging one of said blades, restraining displacement of one of said blades relative to said block.

7. An instrument according to claim 1 wherein said frame comprises a unitary, annular member.

8. An instrument according to claim 1 wherein said frame comprises a unitary member having a polygonal configuration.

9. An instrument according to claim 1 wherein the second end section of each of said blades is pivotally connected to an outer portion of said frame, said intermediate section of each blade extends to one side of said frame and into the opening thereof and said first end section thereof extends along said centerline.

* * * * *